(12) United States Patent
Emeta et al.

(10) Patent No.: US 9,180,229 B2
(45) Date of Patent: *Nov. 10, 2015

(54) ANTIMICROBIAL POLYMER COMPOSITIONS AND THE USE THEREOF

(75) Inventors: Modesto Emeta, Princeton Junction, NJ (US); Robert Di Luccio, Asbury, NJ (US)

(73) Assignee: Ethicon, Inc., Somerville, NJ (US)

(*) Notice: Subject to any disclaimer, the term of this patent is extended or adjusted under 35 U.S.C. 154(b) by 1208 days.

This patent is subject to a terminal disclaimer.

(21) Appl. No.: 11/132,992

(22) Filed: May 19, 2005

(65) Prior Publication Data

US 2006/0263330 A1 Nov. 23, 2006

(51) Int. Cl.
*A61L 31/16* (2006.01)
*A01N 59/16* (2006.01)
*A61L 31/10* (2006.01)

(52) U.S. Cl.
CPC .............. *A61L 31/16* (2013.01); *A01N 59/16* (2013.01); *A61L 31/10* (2013.01); *A61L 2300/102* (2013.01); *A61L 2300/104* (2013.01); *A61L 2300/404* (2013.01)

(58) Field of Classification Search
CPC ...... A61L 17/145; A61L 17/12; A01N 59/16; A01N 25/10; A01N 37/36
See application file for complete search history.

(56) References Cited

U.S. PATENT DOCUMENTS

| | | | |
|---|---|---|---|
| 3,284,417 A | | 11/1966 | Hostettler |
| 3,942,532 A | * | 3/1976 | Hunter et al. ................ 606/231 |
| 4,095,600 A | | 6/1978 | Casey et al. |
| 4,122,129 A | | 10/1978 | Casey et al. |
| 4,181,786 A | * | 1/1980 | Mune et al. .................... 525/161 |
| 4,201,216 A | | 5/1980 | Mattei |
| 4,289,873 A | | 9/1981 | Kubo et al. |
| 4,994,074 A | | 2/1991 | Bezwada et al. |
| 5,644,002 A | | 7/1997 | Cooper et al. |
| 5,668,288 A | | 9/1997 | Storey et al. |
| 6,153,210 A | * | 11/2000 | Roberts et al. ................ 424/411 |
| 6,878,757 B2 | | 4/2005 | Roby |
| 6,881,766 B2 | | 4/2005 | Hain |
| 2004/0127676 A1 | | 7/2004 | Cazaux |
| 2004/0153125 A1 | | 8/2004 | Roby |
| 2004/0162580 A1 | * | 8/2004 | Hain ............................ 606/229 |
| 2004/0185250 A1 | | 9/2004 | John |
| 2005/0100574 A1 | | 5/2005 | Furukawa et al. |
| 2007/0031503 A1 | * | 2/2007 | Hirakura et al. .............. 424/490 |

FOREIGN PATENT DOCUMENTS

| | | |
|---|---|---|
| EP | 0437095 A | 8/1999 |
| WO | WO 96/01231 A | 1/1996 |
| WO | WO 2004/052314 A2 | 6/2004 |
| WO | WO 2004/054503 A2 | 7/2004 |
| WO | 2005/049101 | 6/2005 |
| WO | 2006125125 A2 | 11/2006 |

OTHER PUBLICATIONS

Purification of Laboratory Chemicals (Butterworth-Heinemann, Elsevier, 5th Edition, 2003, p. 84).*
Bendix, Dieter. "Chemical synthesis of polylactide and its copolymers for medical applications." Polymer Degradation and Stability 59.1 (1998): 129-135.*
Multanen M. et al.: "Bacterial Adherence to Silver Nitrate Coated Poly-L-Lactic Acid Urological Stents in Vitro." Urological Research Oct. 2000, vol. 28, No. 5, Oct. 2000, pp. 327-331, XP002451300.
Multanen Markku et al.: "Biocompatibility Encrustation and Biodegredation of Ofloxacine and Silver Nitrate Coated Poly-I-Lactic Acid Stents in Rabbit Urethra" Urological Research, vol. 30, No. 4, Sep. 2002 pp. 227-232, XP002451301.
Multanen M. et al.: "Biocompatibility of Silver Nitrate and Ofloxacine Coated Bioabsorbable SR-PLLA Rods." Urological Research, vol. 29, No. 2, Apr. 2001, pp. 113-117, XP002451302.
Bhargava, H. et al., American Journal of Infection Control, 209-218 (1996).
U.S. Appl. No. 12/688,435, filed Jan. 15, 2010.
CIP U.S. Appl. No. 12/688,435, filed Jan. 15, 2010.

* cited by examiner

*Primary Examiner* — Bethany Barham
*Assistant Examiner* — Peter Anthopolos
(74) *Attorney, Agent, or Firm* — Roberts Mlotkowski Safran & Cole, PC

(57) ABSTRACT

An antimicrobial composition comprising: a complex of an anionic polyester with an antimicrobial metal wherein the anionic polyester has at least one carboxylic acid group. A medical device having an antimicrobial composition comprising: a complex of an anionic polyester with an antimicrobial metal wherein the anionic polyester has at least one carboxylic acid group.

8 Claims, No Drawings

ANTIMICROBIAL POLYMER COMPOSITIONS AND THE USE THEREOF

FIELD OF THE INVENTION

The present invention relates generally to polymer compositions and their use for making or coating articles, such as medical devices. More specifically the invention relates to antimicrobial compositions that are complexes of an anionic polymer with an antimicrobial metal. Further, the present invention relates to complexes of anionic polyester with silver, which may be used alone or in combination with medical devices. The present invention also relates to medical devices utilizing such antimicrobial compositions.

BACKGROUND OF THE INVENTION

Whenever a medical device is used in a surgical setting, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of surgical site infections is often associated with bacteria that colonize on the medical device. For example, during a surgical procedure, bacteria from the surrounding atmosphere may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial metals or metal salts into the medical devices. Such devices desirably provide effective levels of the antimicrobial metal while the device is being used.

For many years silver and silver salts have been used as antimicrobial agents in medical applications. Such medical applications include the use of aqueous silver nitrate solutions to prevent eye infection in newborn babies. Silver salts have also been used to prevent and control infection such as conjunctivitis, urethritis, and vaginitis.

Additionally, silver and silver salts have been used as antimicrobial agents in conjunction with medical devices, such as catheters, cannulae, and stents. Typically, the silver or silver salt is deposited directly onto the surface of the medical device via conventional coating techniques, such as vapor coating, sputter coating, or ion beam coating.

For example, WO 2004054503A2 and U.S. Pat. No. 6,878,757 to Roby describe antimicrobial coatings applicable to sutures where the coating comprises (i) mixtures of caprolactone copolymers and silver stearate, and (ii) mixtures of copolymers of epsilon-caprolactone, bioabsorbable monomer and sodium stearoyl lactylate or the silver salt of stearoyl lactylate, respectively. The silver salt in both of these references remains in a salt form in the copolymer matrix, and silver ions are released into a target environment from the coating by solubilization of the silver salt in the target environment. In turn, the solubility of the silver salt is a function of the nature of environment where it is delivered, and factors such as counter-ion concentration and ionic strength of the target environment.

U.S. Pat. No. 6,881,766 to Hain describes sutures fabricated from and/or coated with compositions including water-soluble glass. The water-soluble glass optionally includes a therapeutic agent, e.g., silver, to promote wound repair. The silver in this case may be incorporated in the form of an inorganic silver salt such as silver oxide, silver nitrate or silver orthophosphate. Similar to the reference described above, the release of the silver ions into the target environment may be dependent upon the solubility of the silver salt in the target environment.

Other metals, such as zinc, copper, magnesium and cerium, have also been found to possess antimicrobial properties, both alone and in combination with silver, some of which exhibited synergistic benefits of their combinations. These and other metals have been shown to provide antimicrobial behavior even in minute quantities.

Other methods of coating antimicrobial metals or metal salts onto a substrate involve deposition or electro-deposition of the metal or metal salt from solution. Additional techniques for incorporating metal into a medical device include dipping, spraying or brushing a liquid solution of the metal or metal salt onto a polymer, for example, in pellet form, prior to processing the medical device. Alternatively, a solid form of the metal or metal salt can be mixed with a finely divided or liquefied polymeric resin, which is then molded into the article. Also, the metal or metal salt can be mixed with monomers of the material prior to polymerization.

However, problems associated with medical devices having metal or metal salts deposited thereon by conventional incorporation techniques include poor adhesion of the metal or metal salt on the medical device, and lack of uniformity in the concentration of the metal or metal salt throughout the coating. Also, it is believed that deposition or electro-deposition of the antimicrobial metal onto a medical device produces coatings that do not release the metal from the coating easily, and therefore require direct contact with microbes in the tissue to have an antimicrobial effect.

Therefore, there is a need to provide an antimicrobial composition where the release mechanism of metal ions into the target environment is not dependent upon solubilization in the target environment. More particularly, there is a need for an antimicrobial composition that exhibits immediate activity upon contact with fluids in the human body. Additionally, it is desirable to have an antimicrobial composition that adheres well to medical devices, as well as antimicrobial medical devices having a uniform distribution of metal or metal salts throughout.

SUMMARY OF THE INVENTION

The present invention is directed to an antimicrobial composition comprising a complex of an anionic polyester with an antimicrobial metal wherein the anionic polyester is selected from the group consisting of an anionic polyester having at least one carboxylic acid group; a sulfonic acid polymer; and a phosphoric polymer.

More specifically, described herein is an antimicrobial composition comprising a complex of an anionic polyester with an antimicrobial metal, wherein the anionic polyester has at least one carboxylic acid group and the formula:

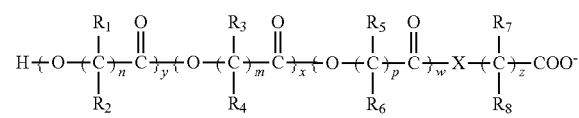

where $800 \geq x+y+w \geq 5$; $y \geq 0$; $x \geq 0$; $w \geq 0$; n, m, p and z independently range from about 1 to about 12; $R_1$, $R_2$, $R_3$, $R_4$, $R_5$, $R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

Additionally, described herein is an antimicrobial composition comprising a complex of an anionic polyester with an antimicrobial metal, wherein the anionic polyester has the formula:

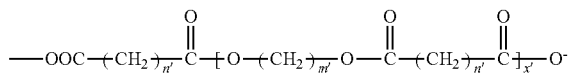

wherein $1>=n'<=13$; $1>=m'<=9$; and x' is the degree of polymerization and ranges from about 4 to about 50.

DETAILED DESCRIPTION

The present invention provides an antimicrobial composition comprising a complex of an anionic polymer with an antimicrobial metal. In one embodiment, the antimicrobial composition comprises a complex of an anionic polyester with an antimicrobial metal, wherein the anionic polyester has at least one carboxylic acid group that may be linear or branched. The complex typically comprises from about 0.05 wt. % to about 50 wt. % of the antimicrobial metal.

The term "complex" as used herein refers to an intimate mixture at the molecular scale, preferably with ionic or covalent bonding between the antimicrobial metal and the anionic polymer. The complex preferably comprises a salt formed between the anionic polymer and metal ions, but it may also comprise metal clusters and/or colloidal metal, for example produced by exposure of the complex to light.

The anionic polymer described herein may be an anionic polyester having at least one carboxylic acid group that may be linear or branched; a sulfonic acid polymer; or a phosphoric acid polymer and the like.

The anionic polyester may be absorbable or nonabsorbable, and may be synthesized via ring opening polymerization of aliphatic lactone monomers. Specifically, the aliphatic lactone monomers are polymerized in the presence of an organometallic catalyst and an initiator. Alternatively, the anionic polyester may be synthesized by condensation polymerization of a diol with diacid, wherein the molar ratio of the diol to the diacid is less than 1. Alternatively, the anionic polyester may be a synthesized anionic form of the reaction product of (a) a polyglycolic acid composition and (b) a polyester of diglycolic acid and a unhindered glycol, as described in more detail in U.S. Pat. Nos. 4,122,129 and 4,095,600, the content each of which is incorporated by reference as if set forth in its entirety; or a synthesized anionic form of the reaction product of (a) an aliphatic polyester of lactide, glycolide, epsilon-caprolactone, p-dioxanone, and trimethylene carbonate and (b) a poly(alkylene diglycolate) homopolymer or copolymer, as described in more detail in U.S. Pat. No. 5,644,002, the content of which is incorporated by reference as if set forth in its entirety.

Typical aliphatic lactone monomers that may be utilized to synthesize the anionic polyester described herein, and from which the repeat units of the anionic polyester are derived, are selected from the group consisting of glycolide, trimethylene carbonate, L-lactide, D-lactide, DL-lactide, mesolactide, epsilon-caprolactone, p-dioxanone, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicyclooctane-7-one and combinations thereof.

The organometallic catalysts include titanates and zirconates, and preferably organotin compounds such as stannous chloride and stannous octoate.

The initiators are desirably compounds containing at least one anionic group, such as a carboxylic acid group, and at least one other group such as a hydroxyl group or an amine. Typical initiators, suitable for the synthesis of an anionic polyester having carboxylic acid groups, are alpha-hydroxyl acids such as glycolic acid, D-lactic acid, DL-Lactic acid, L-lactic acid; β-hydroxyacids, γ-hydroxyacids, δ-hydroxyacids, and ε-hydroxyacids such as ε-hydroxycaproic acid. Preferable initiators contain at least one carboxylic acid group and a primary hydroxyl group, such as glycolic acid. The alcohol group readily participates in a reaction that incorporates the initiator in the growing chain. Typical initiators suitable for the synthesis of branched polyesters with at least one carboxylic acid group are the polyhydroxyacids, such as glucoronic acid.

In certain embodiments, the anionic polyester may have only one carboxylic acid group. Such anionic polyesters are described in U.S. Pat. Nos. 4,201,216 and 4,994,074, the entire content which is incorporated herein by reference, and may be generally represented by the following formula:

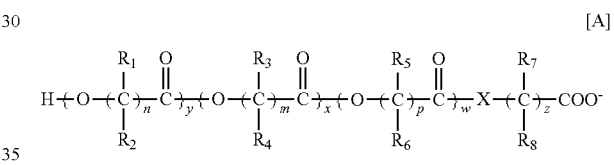

[A]

where $800=>x+y+w>=5$; $y>=0$; $x>=0$; $w>=0$; n, m, p and z independently range from about 1 to about 12; $R_1$, $R_2$, $R_3$, $R_4$, $R_5$, $R_6$ are independently H or a linear or branched alkyl group having from about 1 to about 12 carbon atoms; X is either —O— or —NH—; and $R_7$ and $R_8$ are independently H, a linear or branched alkyl group having from about 1 to about 12 carbon atoms, or a —COOH group.

The anionic polyesters include homopolymers and copolymers of lactide and glycolide, i.e., polylactide, polyglycolide, and copolymers of lactide and glycolide with each other and with other reactive monomers; poly (p-dioxanone); poly (alkylene oxalate); copolymers of vinyl acetates with unsaturated carboxylic acids such as crotonic, acrylic and methacrylic acids; and mixtures of such polymers. Particularly preferred polymers are the copolymers of lactide and glycolide, which contain from about 15 to 85% lactide, and have an inherent viscosity of from about 0.5 to 4.0 measured as a 0.1 percent solution in hexafluoroisopropanol at 25° C. These polymers are water-insoluble, rapidly absorbable, and soluble in many common organic solvents such as acetone, chloroform, toluene, xylene, and 1,1,2-trichloroethane.

It is also possible to produce other anionic polyesters in a similar fashion with terpolymers, tetramers, and the like, from building blocks including, but not limited to, glycolide, lactide, epsilon-caprolactone, trimethylene carbonate, and p-dioxanone.

Specific examples of such anionic polyesters are represented by formulae IA, IIA and IIIA.

The anionic polyester of Formula IA is a copolymer of epsilon-caprolactone and glycolide that is formed by using glycolic acid as an initiator and stannous octoate as the catalyst. The polymerization may be conducted in a batch process that allows the formation of a random copolymer. However, it is also possible to conduct the polymerization in such a way as to allow for the formation of a semi-block copolymer. The initiator ratio may be varied to allow one to obtain a molecular weight that makes the final copolymer in a useable form. The term "initiator ratio" as used herein, refers to the total moles of monomer divided by the total moles of initiator. For example, the initiator ratio may range from about 5 to about 600, corresponding to a Mn of about 575 to about 69,000, respectively. When the anionic polyester is used to prepare a coating on a substrate such as a medical device, the initiator ratio may range from about 10 to 30, corresponding to a Mn of about 1,150 to about 3,450, respectively. The size of the copolymer can vary greatly depending on its ultimate application.

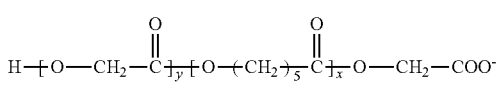

[IA]

anionic α-hydroxy, ω-carboxy poly(ε-caprolactone co-glycolide) where x ranges from about 5 to about 190; y ranges from about 5 to about 190; and x+y<=200.

The anionic polyester represented by Formula IIA is a poly-(epsilon-caprolactone) that is polymerized with glycolic acid as an initiator, and is consequently terminated with a carboxylic acid group. For example, the initiator ratio may range from about 5 to about 600, corresponding to a Mn of about 575 to about 69,000, respectively. When the anionic polyester is used to prepare a coating on a substrate such as a medical device, the initiator ratio ranges from about 10 to about 30, corresponding to a Mn of about 1,150 to about 3,450, respectively.

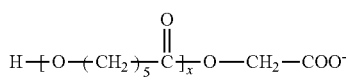

[IIA]

anionic α-hydroxy, ω-carboxy poly(ε-caprolactone where x ranges from about 10 to about 200.

The anionic polyester represented by Formula IIIA is a copolymer formed from lactide and glycolide with glycolic acid as an initiator. The initiator ratio ranges from about 10 to about 200, which corresponds to a Mn of about 1,170 to about 28,800, respectively.

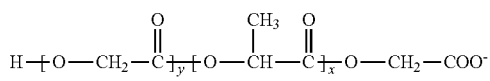

[IIIA]

anionic α-hydroxy, ω-carboxy poly(glycolide co-lactide) where x ranges from about 5 to about 190; y ranges from about 5 to about 190; and
x+y<=200.

Where the number of carboxylic acid groups is desirably 2 or more, one can provide an initiator that will cause the anionic polyester to form, for example, a branched structure. Examples of such initiators include, but are not limited to, tartaric acid, citric acid and the like. The branched structure may have one or more carboxylic acid groups in one or more branches on the polymer backbone or side chain. They may even be in the form of a dendrimer or star structure.

In an alternative embodiment, the anionic polyester may have more than one carboxylic acid groups as represented by Formula A'. For example, copolymers of adipic acid and 1,4 butanediol disclosed in U.S. Pat. No. 3,942,532 may be synthesized in an anionic form as represented by Formula IVA', which is an anionic polyester that is rich in carboxylic acid groups and adipate.

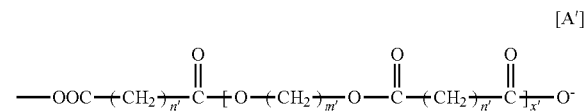

[A']

wherein 1>=n'<=13; 1>=m'<=9; and x' is the degree of polymerization and ranges from about 4 to about 50.

A specific example of such an anionic polyester is polytetramethylene adipate diacid represented by Formula IVA'

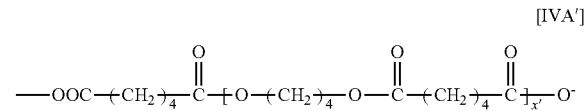

[IVA']

where x' ranges from about 4 to about 50. The value of x' depends on the molar ratio of diol to diacid and the extent of the conversion of the limiting reactant, where the molar ratio of the diol to the diacid is less than 1.

Examples of the diol that may be used to synthesize the anionic polyester of Formula IVA' include, but are not limited to, ethylene glycol, propylene glycol, butanediol, pentanediol, hexanediol, nonanediol, decanediol, undecanediol, dodecanediol, or mixtures thereof. Examples of the diacid include, but are not limited to, succinic, glutaric, adipic, pimelic, suberic, azelaic, sebacic acid, or mixtures thereof. The diols and diacids, upon reaction, may be condensed to obtain a polyester suitable for application as, for example, a substrate coating. Polyesters of the Formula A' may have a molecular weight in the range of approximately 200 to 10,200, preferably 1,000 to 15,000.

The antimicrobial metals (M) referred to herein are metals having antimicrobial efficacy, including but not limited to Ag, Au, Pt, Pd, Ir, Sn, Cu, Sb, Bi, Zn, Ni, Mg, Mn The source of the antimicrobial metal in the complex with the anionic polymer includes, but is not limited to, elemental metals, metal compounds, alloys or mixtures thereof.

Silver is especially potent as an antimicrobial metal against a broad spectrum of microorganisms. Preferably, the source of the antimicrobial metal in the complex with the anionic polymer is elemental silver, silver alloys, a silver compound or mixtures thereof. The silver compound referred to herein is a compound comprising a silver ion, linked to another molecule via a covalent or non-covalent linkage. Examples of silver compounds include, but are not limited to, silver salts formed by silver ion with organic acids (e.g. acetic acids and fatty acids) or inorganic acids, such as silver sulfadiazine ("AgSD"), silver oxide ("Ag$_2$O"), silver carbonate ("Ag$_2$CO$_3$"), silver deoxycholate, silver salicylate, silver iodide, silver nitrate ("AgNO$_3$"), silver paraminobenzoate, silver paraminosalicylate, silver acetylsalicylate, silver ethylenediaminetetraacetic acid ("Ag EDTA"), silver picrate, silver protein, silver citrate, silver lactate, silver acetate and silver laurate.

The complex of an anionic polyester and an antimicrobial metal may be made by treating an anionic polyester with a solution of the source of the antimicrobial metal. For example, the anionic polyester may be in the form of solid fibers, sheet, sponge or fabric. In certain embodiments, the anionic polyester is an ion exchanger. In other embodiments, the anionic polyester may be in free acid form, in which case for example, the source of the antimicrobial metal may be a salt of a weak acid, whereby the anionic polyester is at least partially complexed by the metal salt. When using silver salts of weak acids, for example, the silver ion is exchanged for a proton on the anionic polyester and part of the salt is converted to a weak acid. The mixture of weak acid and salt in the solution results in a buffered solution which maintains a fairly constant pH and controls the degree of exchange reaction. An equilibrium reaction is established whereby the silver ions are bound to the acid portion of the polyester and also to the salt molecules. Similar processes are described in EP-A-0437095, the entire content of which is expressly incorporated herein by reference.

The exchange reaction can be carried out in water or alcohol alone but is preferably carried out in mixtures of water and alcohols. The use of a mixture of water and alcohol provides good solubility for weak acid salts, and the alcohol enhances the ability of the anionic polyester to swell during the exchange reaction. Thus the physical properties (e.g. the inherent mechanical strength) of the anionic polyester are retained. Isopropyl alcohol is the preferred alcohol because many of the above-mentioned silver salts have good solubility therein in combination with water. Preferably, the alcohol to water molar ratio is in the range of about 9:1 to 1:9. If the solution becomes too rich in alcohol, some salts may no longer be soluble particularly if the alcohol is other than methanol. Linear and branched C2-C12 mono- or polyalcohols, including, but not limited to, n-propyl alcohol and ethanol, are suitable alcohols.

The amount of metal salt used is generally about equal to or up to twice the stoichiometric amount of carboxylic acid content of the polyester. Alternatively, a second charge of a stoichiometric amount of metal salt can be used if the reaction is recharged with fresh solvent and salt after the first charge reaches a constant pH. The material with elevated pH is then washed to remove the excess metal salt and ions therefrom.

The present invention provides an antimicrobial composition comprising a complex of an anionic polyester with an antimicrobial metal, wherein the complex comprises from about 0.05 wt. % to about 50 wt. % of metal, and preferably from about 10 wt. % to about 40 wt. % of metal, more preferably from about 18 wt. % to about 35 wt. % of metal.

Accordingly, the complexes of the anionic polyesters previously described in Formulae A, A', and IA to IVA and the antimicrobial metal, are represented by the following:

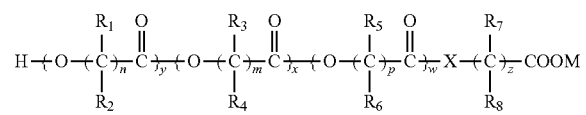
[B]

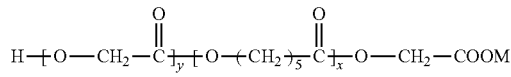
[IB]

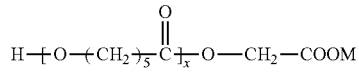
[IIB]

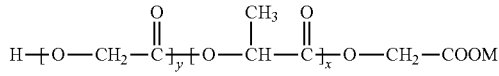
[IIIB]

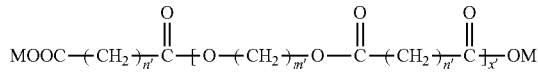
[B']

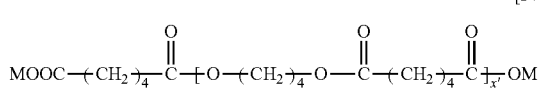
[IVB']

The antimicrobial composition of the present invention provide the advantage of varying release kinetics for the antimicrobial metal ions. These varying release kinetics allow for an initial release of antimicrobial metal that provides antimicrobial activity immediately upon insertion in an aqueous environment, followed by a continual, extended release of the antimicrobial metal from the composition, resulting in sustained antimicrobial activity over time for at least 12 days.

In a further aspect, the antimicrobial composition may optionally contain other components that improve the antimicrobial effectiveness of the composition, or that otherwise serve as active agents for other benefits. These components include, but are not limited to, additional antimicrobials, additional salts, any other excipients or active ingredients that provide the compositions with beneficial properties or enhance the antimicrobial activity of the compositions. Such components include, but are not limited to, antimicrobial agents, antibiotics, and other active ingredients.

The antimicrobial compositions described herein may be used to coat substrate materials. Additionally, they can be a part of the coating that contains the antimicrobial composition described herein. These coatings may comprise either a single layer or multiple layers. In another embodiment, the antimicrobial composition may also be applied to a preformed article or part of an article of manufacture as a coating. The coated article may be produced, for example, by dipping the article into the composition, coextruding the article, wire coating the article, or spraying the article with the composition and then drying the coated article.

The antimicrobial composition may be made separately, and then applied as a coating to a substrate such as a medical device. Alternately, the antimicrobial composition may be made in situ, for example, by first coating a substrate such as a medical device with the anionic polyester followed by in situ treatment with a solubilized salt of the antimicrobial metal, thus imparting antimicrobial properties to the substrate. Additionally, organic liquids such as organic solvents may be utilized to facilitate complexation of the antimicrobial metal and the anionic polyester.

The antimicrobial compositions described herein are used alone or in combination with other polymer coatings to provide advantageous properties to the surface of the substrate. These compositions can also be used, to deliver pharmaceutical agents that, for example, are antiinfective, anticoagulants, improve healing, are antiviral, antifungal, antithrombogenic or impart other properties to coated substrates.

The antimicrobial compositions are also used to inhibit algae, fungal, mollusk, or microbial growth on surfaces. The antimicrobial compositions described herein may also used as herbicides, insecticides, antifogging agents, diagnostic agents, screening agents, and antifoulants.

In another aspect, the present invention includes an article of manufacture that is a medical device that comprises the antimicrobial compositions described herein. In one embodiment, the antimicrobial composition can be used to form an article or a portion of the article, for example by spinning, molding, casting, or extrusion. The antimicrobial composition can be utilized to manufacture a medical device including, but not limited to a fiber, mesh, powder, microspheres, flakes, sponge, foam, fabric, nonwoven, woven mat, a film, suture anchor device, suture, staple, surgical tack, clips, plate and screw, drug delivery device, adhesion prevention barrier, and tissue adhesive.

The medical device may be composed of one or more of the antimicrobial compositions of the present invention, alone or in combination with other polymeric components.

As discussed above, the antimicrobial metal may be incorporated into the anionic polyester in an aqueous alcohol environment. The term "incorporate", "incorporated", or "incorporating", as used herein, refers to combining the antimicrobial metal with the anionic polyester by physical or chemical means. In one embodiment, the antimicrobial metal may be incorporated into the anionic polyester prior to forming a substrate such as a medical device. In an alternative embodiment, the antimicrobial metal can be incorporated into the anionic polyester after the formation of a substrate such as a medical device. For instance, the anionic polyester may be impregnated with the antimicrobial metal by dipping, soaking, spraying or coating a medical device with the antimicrobial metal dispersed in an aqueous alcohol environment, as shown in Examples 1 to 4.

EXAMPLE 1

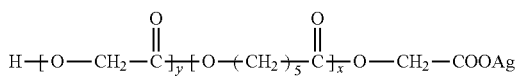

An anionic polyester was prepared by the polymerization of epsilon-caprolactone and glycolide, using glycolic acid as an initiator and a catalyst in the amounts given below:

| | |
|---|---|
| epsilon-caprolactone | 1.8208 moles |
| glycolide | 0.1789 moles |
| glycolic acid | 0.0666 moles (Initiator ratio 30) |
| catalyst: | Stannous octoate 0.33 molar in toluene |

The anionic polyester was dissolved in ethyl acetate to make a 7% solids solution. Thereafter, a size 2/0 polyglactin 910 suture was immersion coated and air dried. The suture had 2.716 weight % coating.

In a bottle covered with aluminum foil, 201 grams of deionized water and 8 grams of isopropanol were mixed. Thereafter, 1.462 grams of silver acetate was added to the aqueous alcohol solution and mixed with a magnetic stirrer for 1½ hours. 20 more grams of isopropyl alcohol was added and mixed to produce a silver salt solution. The size 2/0 coated polyglactin 910 suture was immersed in a 50 gram aliquot of the silver salt solution at room temperature for 5 hours. The suture was rinsed by immersion in deionized water and vacuum dried at room temperature to produce a suture having the antimicrobial composition as a coating thereon. The amount of silver in the complex of the anionic polyester and silver was 34% by weight based on the weight of the anionic polyester.

Silver has a minimum inhibitory concentration (MIC) against *E. Coli* of 10 ppm, as measured in a suitable growth medium and as described by Bhargava, H. et al in the American Journal of Infection Control, June 1996, pages 209-218. The MIC for a particular antimicrobial agent and a particular microbe is defined as the minimum concentration of that antimicrobial agent that must be present in an otherwise suitable growth medium for that microbe, in order to render the growth medium unsuitable for that microbe, i.e., the minimum concentration to inhibit growth of that microbe.

A demonstration of this MIC is seen in the disk diffusion method of susceptibility. A filter paper disk, or other object, impregnated with a pre-selected amount of a particular antimicrobial metal is applied to an agar medium that is inoculated with the test organism. The antimicrobial metal diffuses through the medium, and as long as the concentration of the antimicrobial metal is above the minimum inhibitory concentration (MIC), none of the susceptible microbe will grow on or around the disk for some distance. This distance is called a zone of inhibition. Assuming the antimicrobial metal has a diffusion rate in the medium, the presence of a zone of inhibition around a disk impregnated with an antimicrobial agent indicates that the organism is inhibited by the presence of the antimicrobial metal in the otherwise satisfactory growth medium, the diameter of the zone of inhibition is inversely proportional to the MIC.

The antimicrobial efficacy was evaluated by zone of inhibition assay, in which the sutures were cut into a 5 cm section. A Petri dish containing nutrient agar inoculated with about $10^5$ cfu/ml. A portion of 20 ml of TSA tempered at 47° C. was added into the Petri dish. The inoculum was mixed thoroughly with the growth medium and the suture was placed in the middle of the dish. The inoculated dish was incubated at 37° C. for 48 hr and the zone of inhibition was measured with a digital caliper.

The zone of inhibition assay was performed against *E. coli* over a two-day period. The results indicate that the suture having the complex as a coating thereon exhibited a zone of inhibition against *E. Coli* of 4.5 mm that was sustained for 12 days.

EXAMPLE 2

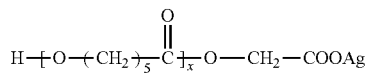

A polycaprolactone polymer containing a carboxylic acid group was prepared utilizing glycolic acid as an initiator and a catalyst in the amounts given below:

| | |
|---|---|
| epsilon-caprolactone | 5000 grams |
| glycolic acid | 111.048 grams |
| catalyst: | Stannous octoate 0.33 molar solution in toluene |

The anionic polyester had a molecular weight Mw=6600 and an inherent viscosity in HFIP of 0.4 dl/g.

The anionic polyester was dissolved in ethyl acetate to make a 7% solids solution. Thereafter, a size 0 braided polyester suture was dipped into the anionic polyester/ethyl acetate solution, and the ethyl acetate was evaporated thereafter. The coating content of the suture was 2.65% by weight.

The anionic polyester coated suture was immersed in isopropanol for 10 minutes. Thereafter, it was immersed for 6 hours in a silver acetate water solution containing 0.943% silver acetate and 4.716% isopropanol. The suture was then washed with deionized water and vacuum dried to produce a suture having the antimicrobial composition as a coating thereon. The amount of silver in the complex of the anionic polyester and silver was 28 by weight based on the weight of the anionic polyester.

The antimicrobial efficacy was evaluated by a zone of inhibition assay as described in Example 1. The zone of inhibition assay was performed against E. coli over a two-day period. The results indicate that the suture having the complex as a coating thereon exhibited a zone of inhibition against E. Coli of 6.8 mm after 24 hours.

EXAMPLE 3

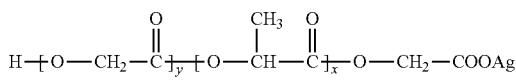

A 65/35 lactide/glycolide anionic polyester was prepared using glycolic acid initiator at a monomer to initiator mole ratio of 15. The catalyst was a 0.33 molar solution of stannous octoate in toluene. A monomer/catalyst mole ratio of 25,000 was used.

The reactant amounts were:

| L(-) lactide | 1.3 moles |
| --- | --- |
| Glycolide | 0.7 moles |
| Glycolic acid | 0.0666 moles |
| Catalyst: | Stannous octoate solution |
| | 0.33 molar solution of toluene |

A coating dispersion of the anionic polyester and calcium stearate in ethyl acetate (4.5 weight % copolymer and 4.5 weight % calcium stearate) was prepared with high shear mixing. A size 2/0 uncoated polyglactin 910 suture was dip coated in the suspension and the ethyl acetate was evaporated. The coating content of the suture was 4.07% by weight.

The anionic polyester coated suture was immersed for 5 hours in a silver acetate water solution containing 0.634% silver acetate and 12.18% isopropyl alcohol. It was washed with deionized water and vacuum dried to produce a suture having the antimicrobial composition as a coating thereon. The amount of silver in the complex of the anionic polyester and silver was 26.7% by weight based on the weight of the anionic polyester.

The antimicrobial efficacy was evaluated by a zone of inhibition assay as described in Example 1. The zone of inhibition assay was performed against E. coli over a two-day period. The results indicate that the suture having the complex as a coating thereon exhibited a zone of inhibition against E. Coli of 1.7 mm after 24 hours.

EXAMPLE 4

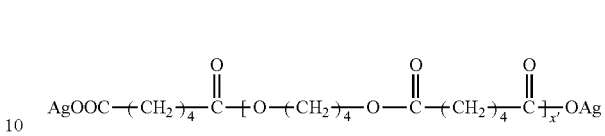

An anionic polyester was prepared by reacting 1,4-butanediol and adipic acid at a molar ratio of 0.8 in the amounts given below:

| Adipic acid | 1.3745 moles |
| --- | --- |
| 1,4-butanediol | 1.0996 moles. |

Thereafter, a size 0 polyester suture is coated with a solution of polytetramethylene adipate in ethyl acetate. The carboxylic acid content of the polytetramethylene adipate was about 2 meq/g. After evaporation of the ethyl acetate, the suture was immersed for 3 hours at room temperature in a silver acetate water solution containing 0.934% silver acetate and 7.47% isopropanol. The suture was washed with deionized water and was vacuum dried to produce a suture having the antimicrobial composition as a coating thereon. The coating content was about 4.6% by weight. The amount of silver in the complex of the anionic polyester and silver was 43% by weight based on the weight of the anionic polyester.

The antimicrobial efficacy was evaluated by a zone of inhibition assay as described in Example 1. The zone of inhibition assay was performed against E. coli over a two-day period. The results indicate that the suture having the complex as a coating thereon exhibited a zone of inhibition of about 4.3 mm against E. Coli, and about 4.5 mm against Staphylococcus Aureus.

EXAMPLE 5

In this example, the direct conversion of the anionic polyester [A or A'] to a complex of an anionic polymer with an antimicrobial metal [B or B'] is accomplished prior to placement on a substrate such as a medical device. Two samples were prepared, an Inventive Sample that uses the anionic polyester technology of this invention and a second example that uses a non-ionic polyester of the same copolymer.

Inventive Sample

An anionic polyester composed of 90/10 caprolactone/glycolide was synthesized by using a glycolic acid initiator at a molar ratio of monomer to initiator of 43. A film was prepared as follows:

Two grams of the anionic polyester were ground and wetted with 0.3 grams of isopropanol. The solids were then admixed with a silver acetate water solution, containing 0.0619 grams silver acetate in 10 grams of water. After two hours, the a complex of the anionic polymer with silver were recovered by filtration and were dried under vacuum at room temperature. About 1.5 grams of the complex were placed on a Teflon lined 0.010" mold. The mold was kept in an oven at 40° C. for about 10 minutes to facilitate film formation.

Comparative Sample

A nonionic polyester composed of 90/10 caprolatone/glycolide was synthesized by using mannitol as an initiator, as described in U.S. Patent Application 2004/0153125. Silver was added as a salt dispersed into molten nonionic polyester coating and converted into a film. About 1.5 grams of the mixture were placed on a Teflon lined 0.010" mold. The mold was kept in an oven at 40° C. for about 10 minutes to facilitate film formation.

The antimicrobial efficacy was evaluated by a zone of inhibition assay, as described in Example 1 except that the films were cut into 1 sq. cm section. The zone of inhibition assay was performed against *S. aureus, E. coli* and *P. aeruginosa* over a two-day period. The results are shown below.

Zone of Inhibition Test

| Sample | *S. aureus* | *E. coli* | *P. aeruginosa* |
|---|---|---|---|
| (a) 2% Ag ion exch in Cap/Gly | — | ++ | + |
| (b) 2% Ag based on Ag acetate in Cap/Gly | — | + | — |

++ medium inhibition (small but clear zone around test article)
+ low inhibition (unclear clear zone around test article)
— No inhibition (no inhibition zone)
(a) Cap/Gly initiated with Glycolic acid (Inventive Sample)
(b) Cap/Gly initiated with Mannitol (Comparative Sample)

Log Reduction

In this test, one side of the film was exposed to about 2000 CFU/0.5 sq. cm *S. aureus* in 10 ul saline with 20% serum for 60 min. The log reduction is the difference in bacteria count of test articles with or without exposure to *S. aureus*. This test measures the reduction of bacteria population in a short time, in no growth condition.

| Sample | *S. aureus* |
|---|---|
| (a) 2% Ag ion exch in Cap/Gly | 0.5 |
| (b) 2% Ag acetate in Cap/Gly | 0 |

(a) Cap/Gly initiated with Glycolic acid (Inventive Sample)
(b) Cap/Gly initiated with Mannitol (Comparative Sample)

What is claimed is:

1. An antimicrobial composition comprising: a complex of an anionic polyester with ions of an antimicrobial metal wherein the anionic polyester has the formula:

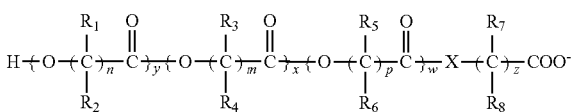

where $800 \geq x+y+w \geq 5$; $y \geq 0$; $x \geq 0$; $w \geq 0$; n, m, p and z independently range from 1 to about 12; $R_1, R_2, R_3, R_4, R_5, R_6$ are independently H or a linear or branched alkyl group having from 1 to about 12 carbon atoms; X is either —O— or —NH—; and $R_7$ and $R_8$ are independently H, a linear or branched alkyl group having from 1 to about 12 carbon atoms, or a —COOH group, and the antimicrobial metal is selected from the group consisting of Ag, Au, Pt, Pd, Ir, Sn, Cu, Sb, Bi, Zn, Ni, and Mn.

2. The antimicrobial composition according to claim 1, wherein the anionic polyester is prepared from a ring-opening polymerization of an aliphatic lactone monomer in the presence of an organometallic catalyst and an anionic initiator.

3. The antimicrobial composition according to claim 2, wherein the aliphatic lactone monomer is selected from the group consisting of glycolide, trimethylene carbonate, L-lactide, D-lactide, DL-lactide, mesolactide, ε-caprolactone, p-dioxanone, 1,3-dioxan-2-one, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, and 6,8-dioxabicycloctane-7-one.

4. The antimicrobial composition according to claim 2, wherein the anionic initiator is selected from the group consisting of alpha-hydroxyl acids, glycolic acid, D-lactic acid, DL-Lactic acid, L-lactic acid; ε-hydroxyacids, γ-hydroxyacids, δ-hydroxyacids, Σ-hydroxyacids, Σ-hydroxycaproic acid, polyhydroxyacids, tartaric acid, citric acid and glucoronic acid.

5. The antimicrobial composition of claim 1, wherein the antimicrobial metal is silver.

6. The antimicrobial composition of claim 5, wherein the amount of silver in the complex is from 0.05% to about 50% by weight based on the weight of the anionic polyester.

7. The antimicrobial composition of claim 5, wherein the amount of silver in the complex is from about 10% to about 40% by weight based on the weight of the anionic polyester.

8. The antimicrobial composition of claim 5, wherein the amount of silver in the complex is from about 18% to about 35% by weight based on the weight of the anionic polyester.

\* \* \* \* \*